United States Patent [19]

Mikkelsen

[11] Patent Number: Plant 5,876

[45] Date of Patent: Feb. 10, 1987

[54] KALANCHOE PLANT NAMED BINGO

[75] Inventor: James C. Mikkelsen, Ashtabula, Ohio

[73] Assignee: Mikkelsens, Inc., Ashtabula, Ohio

[21] Appl. No.: 712,113

[22] Filed: Mar. 15, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Bingo, characterized by its bright pink flower color, floriferous habit, dense and relatively small leaves, early flowering, and its excellent keeping qualities.

1 Drawing Figure

The present invention relates to a new and distinct cultivar of Kalanchoe plant, botanically known as *Kalanchoe blossfeldiana,* and known by the cultivar name Bingo. Bingo was developed by me through controlled breeding by crossing Feuerball (seed parent) and the unpatented culivar Pluto (pollen parent). Feuerball is disclosed in U.S. Plant Pat. No. 3,861.

Asexual reproduction by stem cuttings has shown that the unique features of this new Kalanchoe are stabilized and are reproduced true to type in successive propagations.

The following characteristics distinguish the new Kalanchoe from both its parent culivars and other cultivated kalanchoes of this type known and used in the floriculture industry:

1. Bingo has bright pink flowers which are deeper in color than the flowers of the cultivar Mini-Pluto (not patented) or Dignity (disclosed in U.S. Plant Pat. No. 5,255), the flowers of Dignity being lavender pink. The flowers of Sensation (disclosed in U.S. Plant Pat. No. 4,727) are deeper rose pink. Feuerball, the female parent, has light red flowers.

2. Bingo is greater in height than Mini-Pluto, equal in height to Dignity and Sensation, and is less tall and more compact than Feuerball.

3. Flower size is larger than Mini-Pluto and Feuerball, but equal in size to Dignity and Sensation. Bingo has a rounded petal type similar to Sensation.

4. There are more flowers on the terminal and lateral branches than Mini-Pluto, and approximately as many flowers as Dignity, Sensation and Feuerball.

5. Flowering time is 9 weeks after start of short days in summer, and 11 weeks in winter, which is earlier than Dignity which is 10 weeks in summer, 13 weeks in winter; Sensation is 11 weeks in summer and 14 weeks in winter; Feuerball is 10 weeks in summer and 14 weeks in winter. Mini-Pluto is 7 weeks in summer but equal to Bingo in winter at 11 weeks, all as tested in Ashtabula, Ohio.

6. After flower initiation, plants must be treated with B-9 in all seasons to reduce peduncle elongation.

7. Leaf color is darker green than Mini-Pluto and similar in color to Sensation, Dignity and Feuerball.

8. Leaf shape is oblong like Mini-Pluto, while Dignity, Sensation and Feuerball have ovate leaves.

9. Leaf size of Bingo is slightly larger than Mini-Pluto but smaller than Dignity, Sensation and Feuerball.

10. The moderate growth rate, early flowering and small dark dense foliage of Bingo make the cultivar hightly suited for 10 cm pot production.

11. Bingo is better branched than Feuerball, equal in branching to Sensation and Dignity, but not as well branched as Mini-Pluto.

The accompanying colored photograph, taken in February of 1985, illustrates in perspective view the overall appearance of this cultivar, showing the colors as true as it is reasonably possible to obtain in a colored reproduction of this type.

The following is a detailed description of my new Kalanchoe cultivar grown in 10 cm plastic pots produced under commercial practices in the greenhouses of Mikkelsens Inc., Ashtabula, Ohio, in January and February, 1985. Color references are made to The Royal Horticultural Society Colour Chart except where general terms of ordinary dictionary significance are used.

Parentage: A controlled cross of Feuerball × Pluto.

Propagation:

(A) *Type cutting.*—Short stem cutting up to 2 cm long; propagates easily and in great quantity from stock plants.

(B) *Time to root.*—10 days at 21° C. summer, 14 days at 21° C. winter.

(C) *Rooting habit.*—Many fine fibrous roots.

Plant description:

(A) *Form.*—Short, compact, upright; ideally suited for growing and scheduling practices for 10 cm pots.

(B) *Habit of growth.*—Moderate rate of growth with branching usually from every node.

(C) *Foliage.*—Leaves simple, opposite. (1) Size: Average full grown leaf of plant in flowering in a 10 cm pot is 110 mm long and 70 mm wide. (2) Shape: Elliptic to oblong, apex obtuse to truncate, base attenuate. (3) Texture: Glabrous, coriaceous, succulent. (4) Margin: Crenate. (5) Color: young foliage, top side green 137B, under side green 137C. Mature foliage, top side yellow-green 147B, under side yellow-green 147C.

Flowering description:

(A) *Flowering habits.*—Cyme inflorescence; each shoot is formed by dichotomous branching, starting with the opening of the terminal flower of main axis, followed by terminal flowers of the side branching, continuing with subsequent development of branches in the inflorescence.

Major inflorescence is 60 to 70 mm in diameter and lateral inflorescences are 40 to 50 mm in diameter in a 10 cm pot.

(B) *Natural flowering season.*—Late December. Flowering time under controlled daylength at 20° C. in summer is 9 weeks; in winter is 11 weeks. Flowering time depends on temperature, light intensity, and other growing conditions.

(C) *Flower buds.*—Oblong up to 12 mm long, developing to tubular as flower petals mature, sheathed with four green sepals; corolla at maturity 10 mm long.

(D) *Flowers borne.*—Compound dichasial cymes; peduncle 4 mm in diameter, with peduncle length depending on growing conditions and B-9 application; pedicels up to 9 mm long.

(E) *Quantity of flowers.*—Highly floriferous; main axis counted over 100 flowers, side branches over 50 flowers with 5 or more side branches in a 10 cm pot; excellent keeping quality.

(F) *Petals.*—(1) Shape: Nearly rounded, top cuspidate. (2) Color: Top side when opening red-purple 67C, fading to red-purple 68A; under side 52C; occasional petals showed 52A. (3) Number of petals: Four (4) united in corolla; petals 7 mm in diameter; flower 18 mm in diameter.

(G) *Reproductive organs.*—(1) Stamens: Eight (8 ) in number. (a) Anther shape: Flat elliptical, color yellow. (b) Filament color; Light green. (c) Pollen color: Yellow. (2) Pistels: (a) Stigma: Flat, immature color greenish white, mature color white. (b) Styles: Light green. (c) Ovaries: 4 celled, 5 mm in size, color light green.

Disease resistance: Highly resistant to Mildew. No other disease problems seen to date.

I claim:

1. A new and distinct cultivar of Kalanchoe plant named Bingo, as illustrated and described, and particularly characterized by its bright pink flower color, floriferous habit, dense and relatively small leaves, early flowering, and its excellent keeping qualities.

* * * * *

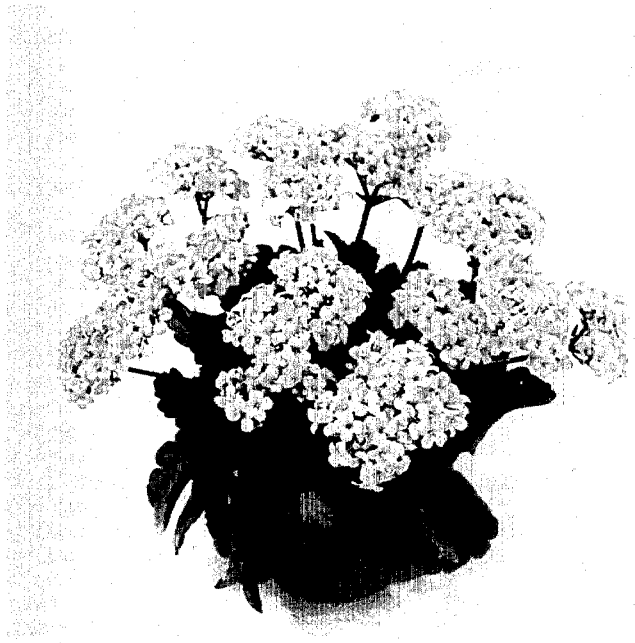

BINGO